United States Patent [19]

Gay

[11] 4,032,617

[45] June 28, 1977

[54] BIS(3,5-DIFLUOROSALICYLALDEHYDE)ETHYLENEDIIMINE-$Co^{+2}$ COMPOUND AND USE

[75] Inventor: Walter A. Gay, Cheshire, Conn.

[73] Assignee: Olin Corporation, New Haven, Conn.

[22] Filed: Dec. 3, 1975

[21] Appl. No.: 636,905

[52] U.S. Cl. .............................. 423/219; 423/579; 260/429 C; 260/429 J; 260/439 R
[51] Int. Cl.² .................. B01D 53/34; C07F 15/06
[58] Field of Search ........................ 423/219, 579; 260/429 J, 429 C, 439 R

[56] References Cited

UNITED STATES PATENTS 2,450,276  9/1948  Fogler et al. ..................... 423/579

OTHER PUBLICATIONS

Calvin et al., The Oxygen–Carrying Synthetic Chelate Compounds, IV, Magnetic Properties, J. Amer. Chem. Soc., vol. 68, Nov. 1946, pp. 2267–2273.

*Primary Examiner*—Earl C. Thomas
*Attorney, Agent, or Firm*—William A. Simons; Thomas P. O'Day; F. A. Iskander

[57] ABSTRACT

A novel compound is described which is useful as a reversible oxygen carrier. This chelate compound is bis(3,5-difluorosalicylaldehyde)ethylenediimine-$Co^{+2}$.

2 Claims, No Drawings

BIS(3,5-DIFLUOROSALICYLALDEHYDE)ETHYLENEDIIMINE-Co$^{+2}$ COMPOUND AND USE

The invention herein described was made in the course of or under a contract or subcontract thereunder, with the United States Air Force.

The present invention is directed to a novel compound and its use. More particularly, the present invention is directed to the compound bis(3,5-difluorosalicylaldehyde)ethylenediimine-C$^{+2}$ and its use as a reversible oxygen carrier.

Synthetic reversible oxygen-carrying chelates have been of interest as a means of separating molecular oxygen from the air and as model compounds for natural oxygen carriers such as hemoglobin. One class of compounds discovered to have these utilities included chelates derived from o-hydroxyaldehydes. Of particular interest was cobaltous bis(salicylaldehyde)ethylenediimine which absorbs oxygen upon exposure to air for several days and desorbs the oxygen upon being heated in a stream of carbon dioxide.

Many other chelating systems have been investigated since the original work and the field has greatly expanded to include chelates no longer containing the hydroxy-aldehyde moiety. These are generally used in solution for homogeneous catalysis and in biological reactions of metal complexes. However, few, if any, match the properties of, for example, cobaltous bis(-salicylaldehyde)ethylenediimine, and exhibit high instability in the solid state as well as an ability to bind other gases in the air, such as hydrogen and carbon dioxide, as well as oxygen. They have, therefore, been placed outside the realm of utility in breathing apparatus and other areas where a reliable oxygen supply is required.

During World War II, the United States Navy investigated the use of cobaltous (bis salicylaldehyde)ethylenediimine derived compounds as a means of producing oxygen aboard a destroyer tender for welding and cutting. The cost of producing oxygen by this means did not exceed that of cylinder oxygen but the project was discontinued due to the shortage of cobalt. More recently these types of compounds have been considered for utility in breathing apparatus in military aircraft as a replacement for the troublesome liquified oxygen (LOX) system. An aircraft oxygen system utilizing cobaltous bis(salicylaldehyde)ethylenediimine has been designed, fabricated, and tested. The system was found to have an initial oxygen delivery rate of 4.7 lbs/hr but the compound activity degraded relatively fast so that after only 100 hours of testing, the delivery rate fell to only 2.8 lbs/hr (less than 60% of initial delivery). As a result of this testing, other compounds were considered for breathing apparatus and development work is being done on, for example, cobalt bis(3-fluoro-salicylaldehyde)ethylenediimine.

A new chelate has now been discovered which exhibits oxygen absorption in an amount close to theoretical and is believed to do so at a promising rate. This new compound may prove to be good breathing apparatus component and has already been proved as a good oxygen absorber-desorber and is useful as a means for removing molecular oxygen from air. This novel compound of the present invention is bis(3,5-difluorosalicylaldehyde)ethylenediimine-Co$^{+2}$ and is referred to in abbreviated language as difluomine.

This novel compound of the present invention is believed to have the following structural formula (I):

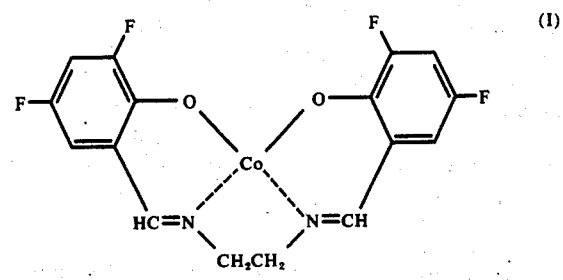

This compound may also be illustrated in the hydrate and oxygenated hydrate form as shown in formulas (II) and (III) respectively as follows:

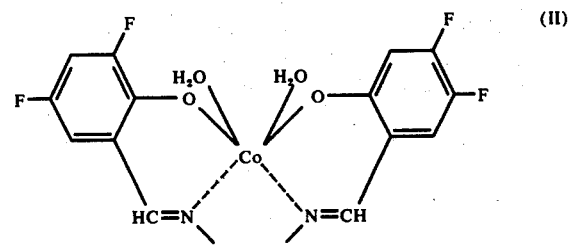

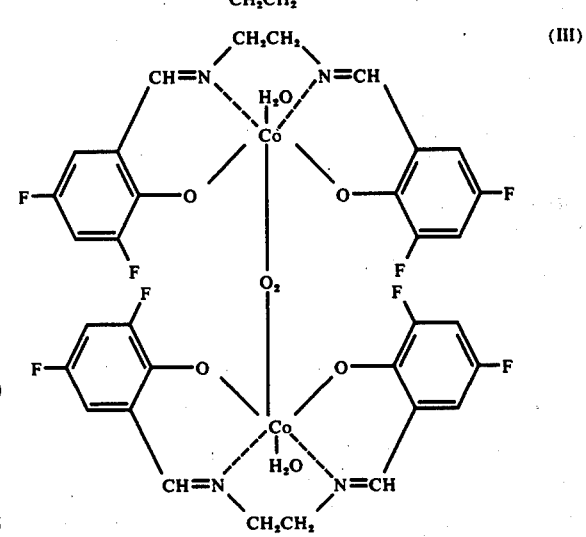

The novel compound of the present invention may be prepared by a method wherein 3,5-difluorosalicylaldehyde is reacted with ethylenediamine in an aqueous solution in the presence of a base, e.g., sodium hydroxide, and e.g., ethanol. The reaction mixture is heated under a nitrogen blanket and a compound such as piperidine, pyridine, or the like is added. The reaction mixture is then brought to reflux temperature and a cobalt-contributing compound, e.g., cobalt chloride hexahydrate, in water is added. the chelate of the present invention presipitates upon the addition of the cobalt-contributing compound. Refluxing is continued until the reaction is completed to a desirable degree or until no further measurable precipitation occurs. The product precipitate, the compound of the present invention, may be isolated by any known solid liquid separation technique, e.g., filtration.

In general about 0.1 to about 2, and preferably about 0.3 to about 0.7 moles of ethylenediamine is used per mole of the salicylaldehyde compound. About 0.4 to about 4.0 and preferably about 0.8 to about 1.5 moles of base, is added per mole of salicylaldehyde compound and most advantageously an equimolar amount is used. The alcohol and water function, at least in part, as solvent for the reactants and there is no criticality to the amounts of these present in the reaction. However, about 5 to about 75% by weight of alcohol, e.g., about 10 to about 50% by weight, may be used based on the total weight of the starting reaction solution, excluding the piperidine or equivalent compound and the cobalt-containing compound which are subsequently added to the reaction solution. About 5 to about 75% by weight, e.g., about 40 to about 70% by weight, of water may be used based on the total weight of the starting reaction solution, excluding the piperidine or equivalent compound and the cobalt-containing compound which are subsequently added thereto.

As mentioned, the reactants in aqueous solution are heated under a nitrogen blanket to initiate reaction. Generally, the reactants are heated to a temperature in the range of about 40° to about 100° C, and preferably about 50° to about 80° C, during which time the peperidine or equivalent compound is added. In general about 0 to about 10 moles of piperidine or equivalent, and preferably about 1 to about 5 moles is added per mole of salicylaldehyde compound. After this, the solution is raised to reflux temperature and the cobalt-contributing compound is added, e.g., in a step-wise fashion. In general about 0.3 to about 3.0 moles of the cobalt-contributing compound and preferably about 0.8 to about 1.2 moles of the cobalt-contributing compound, is used per mole of 3.5-difluorosalicylaldehyde. As mentioned, the desired product begins to precipitate upon addition of the cobalt-containing compound to the reaction mixture, and may subsequently be isolated by conventional techniques.

Among alternative methods of preparing the novel compound of the present invention is the anhydrous approach. The method is similar to that above except that anhydrous components are employed. Thus, anhydrous alcohol may be used as well as an anhydrous base, e.g., an alcoholic solution of sodium ethoxide. Likewise, a cobalt-contributing compound in anhydrous alcohol rather than water, may be used. Because an anhydrous-type product is believed to be obtained by this method, it is believed that, for some utilities of the final product, this method if preferred.

The invention is more fully understood by the following examples. These examples are presented for illustrative purposes and the invention should not be construed to be limited thereto:

EXAMPLES 1 to 3

Three samples of the compound of the present invention were prepared by the following technique:

A reaction mixture of 22.13 g (0.14 mole) 3,5-difluorosalicylaldehyde (XIV), 5.60 g (0.14 mole) sodium hydroxide, 4,26 g (0.071 mole) ethylenediamine, 130.9 g ethanol, and 327 g deionized water was heated to 60° C with stirring under nitrogen and 29.82 g (0.35 mole) piperidine added. The reaction mixture was brought to reflux, and a solution of 17.1 g (0.072 mole) cobalt chloride hexahydrate (<50 ppm nickel) in 49 g deionized water added within 10 minutes. The chelate precipitated immediately. Following a reflux period of 2 hours, the reaction mixture was allowed to cool to room temperature under nitrogen without stirring. The chelate was filtered, washed with 3 × 100 ml deionized water, and dried to a constant weight in vacuum. Yield expressed as difluomine·2$H_2O$ is 92.8% for the first example, and analysis shows 45.32% carbon, 2.82% hydrogen, 6.44% nitrogen, 17.50% fluorine, and 14.40% cobalt.

EXAMPLE 4

The method used in Examples 1 to 3 is repeated except that a mole equivalency amount of pyridine was used in place of the piperidine.

EXAMPLE 5

In this example, anhydrous components were used as follows:

To a stirred reaction mixture of 8.0 g (50.6 mmole) 3.5-difluorosalicylaldehyde (XIV), 1.540 g (25.7 mmole) ethylenediamine, 60 ml anhydrous ethanol, and 90 ml piperidine was added under nitrogen an alcoholic solution of sodium ethoxide prepared from 1.22 g (50.6 mmole) NaH and 48.04 g anhydrous ethanol. At reflux a solution of 3.376 g (26.0 mmole) cobalt chloride hexahydrate in 17.7 g anhydrous ethanol was added in 5 minutes. Crystal formation occurred immediately. After heating at reflux for 2 hours, the reaction mixture was allowed to cool to room temperature without stirring. After filtration and washing with 2 × 50 ml abs ethanol, the chelate was dried to a constant weight of 6.0 g and elemental analysis shows 44.64% carbon, 3.53% hydrogen, 6.77% nitrogen, 13.4% fluorine, and 14.92% cobalt.

The product obtained from Examples 1 to 5 were tested and found to absorb oxygen at room temperature and to desorb oxygen upon heating. the following Table shows the absorption-desorption properties as determined by thermal gravimetric analysis (TGA):

TABLE

| | | Thermal Gravimetric Analysis[4] | | | | | | | | |
|---|---|---|---|---|---|---|---|---|---|---|
| | | SCAN[c] | | ACTIVATION[b] | | | ABSORPTION[b,E] | | | DESORPTION | |
| Example | Chelate[a] | Temp. Range (°C) | Wt. Loss (%) | Temp. (°C) | Time (min) | Wt. Loss (%) | Temp. (°C) | Time (min) | Wt. Gain (%) | Temp. (°C) | Wt. Loss (%) |
| 1 | Difluomine | 20 – 50 | 0 | 104 | 65 | 4.02 | 30 | 55 | 3.87 | — | — |
| | | 50 – 100 | ~5 | 146 | 50 | 4.11 | 30 | 50 | 3.94 | | |
| | | 100 – 290 | 0 | | | | | | | | |
| | | >290 | Decomp. | | | | | | | | |
| 2 | Difluomine | 20 – 65 | 0 | 140 | 50 | 3.86 | 30 | 50 | 3.70 | 140 | 3.90[G] |
| | | 65 – 110 | ~3.9 | | | | 30 | 50 | 3.74 | | |
| | | 110 – 310 | 0 | | | | | | | | |
| | | >310 | Decomp. | | | | | | | | |
| 3 | Difluomine | 20 – 65 | 0 | 140 | 50 | 3.98 | 30 | 60 | 3.54 | 110 | 3.22[F] |
| | | 65 – 110 | ~4.06 | | | | 30 | 60 | 3.52 | | |
| | | 110 – 310 | 0 | | | | | | | | |
| | | >310 | Decomp. | | | | | | | | |
| 4 | Difluomine (pyridine aqueous route) | 20 – 65 | 0 | 150 | 50 | 4.61 | 30 | 60 | 4.00 | 130 | 3.74[G] |
| | | 65 – 95 | ~4.49 | | | | 30 | 60 | 3.51 | | |
| | | 95 – 275 | 0 | | | | | | | | |

TABLE-continued

| Example | Chelate[B] | SCAN[C] Temp. Range (°C) | Wt. Loss (%) | ACTIVATION[D] Temp. (°C) | Time (min) | Wt. Loss (%) | ABSORPTION[D,E] Temp. (°C) | Time (min) | Wt. Gain (%) | DESORPTION Temp. (°C) | Wt. Loss (%) |
|---|---|---|---|---|---|---|---|---|---|---|---|
| 5 | Difluomine (anhydrous route) | >275<br>20 – 65<br>65 – 150<br>110 – 280<br>>280 | Decomp.<br>0<br>~15.2<br>0<br>Decomp. | 150 | 50 | 15.00 | 30<br><br>30 | 60<br><br>60 | 3.47<br><br>3.26 | 120 | 4.17[G] |

A = TGA performed with a Du Pont Model 950 Thermogravimetric Analyzer.
B = Chelate predried to a constant weight in vacuum.
C = Scanned in vacuum to 400 – 500° C.
D = Isothermal conditions under vacuum.
E = Oxygen flow at 100 ml/min.
F = Scanned in $N_2$ at 10° C/min to constant weight.
G = Scanned in vacuum at 10° C/min to constant weight.

What is claimed is:

1. The compound bis(3,5-difluorosalicylaldehyde)ethylenediimine-$Co^{+2}$.

2. In an oxygen absorbing-desorbing process wherein a chelate is used which absorbs oxygen and upon heating desorbs oxygen, the improvement comprising using as a chelate the compound of claim 1.

* * * * *